United States Patent [19]
Youngdale

[11] 4,082,783
[45] Apr. 4, 1978

[54] 2A,2B-DIHOMO-15-ALKYL PGF$_1\alpha$ ANALOGS

[75] Inventor: Gilbert A. Youngdale, Portage, Mich.

[73] Assignee: The Upjohn Company, Kalamazoo, Mich.

[21] Appl. No.: 663,362

[22] Filed: Mar. 3, 1976

Related U.S. Application Data

[62] Division of Ser. No. 511,220, Oct. 2, 1974, Pat. No. 3,974,195.

[51] Int. Cl.$^2$ ................................................ C11C 3/02
[52] U.S. Cl. .................................. 260/410.9 R; 560/9;
560/121; 260/404; 260/404.5; 260/268 R;
260/410; 260/413; 260/326.2; 260/514 D;
260/293.65; 424/305; 424/318; 424/312;
544/69
[58] Field of Search ................... 260/410.9 P, 413 P,
260/404, 404.5 P, 410 P, 468 D; 424/312

[56] References Cited

U.S. PATENT DOCUMENTS 3,514,383  5/1970  Beal et al. ...................... 260/410.9 P

OTHER PUBLICATIONS

Weeks, J., et al., Journal of Pharmacology and Experimental Therapeutics, vol. 186, (1973), pp. 67–74.

*Primary Examiner*—Winston A. Douglas
*Assistant Examiner*—John F. Niebling
*Attorney, Agent, or Firm*—Robert A. Armitage

[57] ABSTRACT

2a,2b-Dihomo-15-methyl and 15-ethyl PGF- and PGE-type compounds are disclosed with process for making them. These compounds are useful for a variety of pharmacological purposes, including anti-ulcer, inhibition of platelet aggregation, increase of nasal patency, labor inducement at term, and wound healing.

7 Claims, No Drawings

2A,2B-DIHOMO-15-ALKYL PGF$_1\alpha$ ANALOGS

The present application is a division of Ser. No. 511,220, filed Oct. 2, 1974, issued on Aug. 10, 1976 as U.S. Pat. No. 3,974,195.

The present invention relates to prostaglandin analogs, the essential material constituting a disclosure of which is incorporated here by reference from U.S. Pat. No. 3,974,195.

I claim:

1. An optically active compound of the formula:

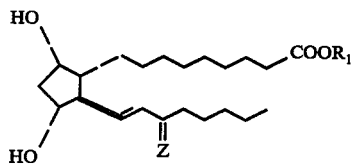

wherein Z is

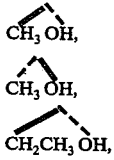

or

and wherein R$_1$ is hydrogen, alkyl of one to 12 carbon atoms, inclusive,

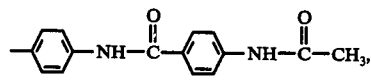

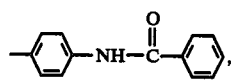

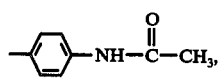

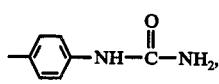

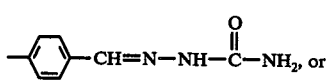

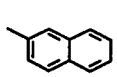

or pharmacologically acceptable salts thereof when R$_1$ is hydrogen.

2. A compound according to claim 1, wherein Z is

3. 2a,2b-Dihomo-15(S)-15-methyl-PGF$_{1\alpha}$, a compound according to claim 2, wherein R$_1$ is hydrogen.

4. 2a,2b-Dihomo-15(S)-15-methyl-PGF$_{1\alpha}$, methyl ester, a compound according to claim 2, wherein R$_1$ is methyl.

5. A compound according to claim 1, wherein Z is

6. 2a,2b-Dihomo-15(R)-15-methyl-PGF$_{1\alpha}$, a compound according to claim 5, wherein R$_1$ is hydrogen.

7. 2a,2b-Dihomo-15(R)-15-methyl-PGF$_{1\alpha}$, methyl ester, a compound according to claim 40, wherein R$_1$ is methyl.

* * * * *